US008540756B2

(12) United States Patent
Olsen et al.

(10) Patent No.: US 8,540,756 B2
(45) Date of Patent: *Sep. 24, 2013

(54) SURGICAL FASTENER AND ASSOCIATED SYSTEMS AND METHODS

(75) Inventors: Russell G. Olsen, Cedar City, UT (US); Steven S. Ramboz, Summit, UT (US)

(73) Assignee: Ortho Vation Medical LLC, Cedar City, UT (US)

( * ) Notice: Subject to any disclaimer, the term of this patent is extended or adjusted under 35 U.S.C. 154(b) by 270 days.

This patent is subject to a terminal disclaimer.

(21) Appl. No.: 12/856,471

(22) Filed: Aug. 13, 2010

(65) Prior Publication Data

US 2011/0270323 A1 Nov. 3, 2011

Related U.S. Application Data

(63) Continuation-in-part of application No. 12/772,716, filed on May 3, 2010.

(51) Int. Cl.
*A61B 17/04* (2006.01)
*A61B 17/86* (2006.01)
*A61F 2/08* (2006.01)

(52) U.S. Cl.
USPC ............ 606/305; 606/308; 411/403; 411/407

(58) Field of Classification Search
USPC ......................... 606/300–321; 411/403, 407
See application file for complete search history.

(56) References Cited

U.S. PATENT DOCUMENTS

| | | | |
|---|---|---|---|
| 954,073 A * | 4/1910 | Bender | 81/454 |
| 1,039,751 A | 10/1912 | Ingram | |
| 2,248,054 A | 7/1941 | Becker | |
| 2,524,095 A | 11/1946 | Williams | |
| 2,445,525 A | 7/1948 | Gulden | |
| 2,496,309 A | 2/1950 | Pugh | |
| 2,570,465 A | 10/1951 | Lundholm | |
| 2,669,896 A | 2/1954 | Clough | |
| 2,954,719 A | 10/1960 | Vaughn | |
| 3,575,080 A | 4/1971 | Hannay | |
| 3,604,487 A | 9/1971 | Gilbert | |
| 3,641,866 A * | 2/1972 | Mortensen | 411/41 |
| 4,140,111 A | 2/1979 | Morrill | |
| 4,149,434 A | 4/1979 | Wilson | |
| 4,202,244 A * | 5/1980 | Gutshall | 411/404 |
| 4,228,723 A | 10/1980 | Cunningham | |
| 4,581,962 A | 4/1986 | Marbourg | |

(Continued)

FOREIGN PATENT DOCUMENTS

WO 9956662 11/1999
WO 2008-140289 A1 11/2008

OTHER PUBLICATIONS

U.S. Appl. No. 12/467,175 Final Office Action dated Jun. 15, 2012.

(Continued)

*Primary Examiner* — Andrew Yang
*Assistant Examiner* — Olivia C Chang
(74) *Attorney, Agent, or Firm* — Kunzler Law Group, PC

(57) ABSTRACT

According to one embodiment, a fastener includes a shank defined about a central axis and a head coupled to the shank. The head includes a continuous receptacle circumscribing the central axis. The continuous receptacle includes a radially inner surface that is angled radially inwardly toward the central axis in a head-to-shank direction.

18 Claims, 10 Drawing Sheets

(56) References Cited

U.S. PATENT DOCUMENTS

| | | | |
|---|---|---|---|
| 4,776,328 A | 10/1988 | Frey et al. |
| 4,911,154 A | 3/1990 | Vickers |
| 5,020,519 A | 6/1991 | Hayes et al. |
| 5,129,901 A | 7/1992 | Decoste |
| 5,139,499 A | 8/1992 | Small et al. |
| 5,214,987 A | 6/1993 | Fenton, Sr. |
| 5,484,440 A | 1/1996 | Allard |
| 5,531,750 A | 7/1996 | Even-Esh |
| 5,649,931 A | 7/1997 | Bryant et al. |
| 5,827,285 A | 10/1998 | Bramlet |
| 5,951,554 A | 9/1999 | Holmes |
| 6,142,957 A | 11/2000 | Diamond et al. |
| 6,162,234 A | 12/2000 | Freedland et al. |
| 6,302,632 B1 | 10/2001 | Lin |
| 6,780,198 B1 | 8/2004 | Gregoire et al. |
| 6,827,722 B1 | 12/2004 | Schoenefeld |
| 6,860,889 B2 | 3/2005 | Bonati et al. |
| 6,921,402 B2 | 7/2005 | Contiliano et al. |
| 6,997,086 B1 | 2/2006 | Graham |
| 7,073,415 B2 | 7/2006 | Casutt et al. |
| 7,090,680 B2 | 8/2006 | Bonati et al. |
| 7,147,421 B2 | 12/2006 | Suzuki |
| 7,204,838 B2 | 4/2007 | Jackson |
| 7,452,361 B2 | 11/2008 | Kreidler |
| 7,494,311 B2 | 2/2009 | Fuerle |
| 7,938,044 B2 | 5/2011 | Ensign |
| 2003/0158555 A1 | 8/2003 | Sanders et al. |
| 2004/0044345 A1 | 3/2004 | DeMoss et al. |
| 2004/0220575 A1 | 11/2004 | Biedermann et al. |
| 2005/0172762 A1 | 8/2005 | Suzuki |
| 2005/0268757 A1 | 12/2005 | Walker |
| 2005/0277923 A1 | 12/2005 | Sweeney |
| 2006/0200147 A1 | 9/2006 | Ensign et al. |
| 2007/0101835 A1 | 5/2007 | Totsu |
| 2007/0123909 A1 | 5/2007 | Rupp et al. |
| 2007/0213732 A1 | 9/2007 | Khanna et al. |
| 2008/0249577 A1 | 10/2008 | Dreyfuss |
| 2009/0054901 A1 | 2/2009 | Oh et al. |
| 2009/0176190 A1 | 7/2009 | Ruiz-Vela et al. |
| 2009/0216282 A1 | 8/2009 | Blake et al. |
| 2009/0257819 A1 | 10/2009 | Burton |
| 2009/0260489 A1 | 10/2009 | Siong |
| 2009/0270927 A1 | 10/2009 | Perrow et al. |

OTHER PUBLICATIONS

U.S. Appl. No. 12/467,175 Notice of Allowance dated Aug. 23, 2012.
PCT/US2011/034968, International Search Report and Written Opinion, Jan. 6, 2012.
U.S. Appl. No. 12/467,175 Office Action, Nov. 23, 2011.
U.S. Appl. No. 12/772,716 Office Action, Jan. 24, 2012.

* cited by examiner

SURGICAL FASTENER AND ASSOCIATED SYSTEMS AND METHODS

CROSS-REFERENCE TO RELATED APPLICATION

This application is a continuation-in-part of U.S. patent application Ser. No. 12/772,716, filed May 3, 2010, which is incorporated herein by reference.

FIELD

This invention relates to fasteners and associated fastening devices and more particularly relates to surgical fasteners and associated installation and removal tools.

BACKGROUND

Specialized fasteners for surgical (e.g., medical) applications are known in the art. In typical surgical applications, these specialized fasteners (e.g., screws) are fastened to the tissue (e.g., bone tissue) of a patient. Surgical fasteners are often used with other devices, such as pins, braces, and plates, in the setting and immobilization of bone fractures, as well as in other applications. Often, conventional surgical fasteners are fastened to the tissue by forming a hole in the tissue at a placement site and threading the fastener into the hole. This procedure commonly requires a medical professional performing the procedure to position the fastener proximate the placement site with one hand and with the other hand articulating an installation tool to drive the fastener into the hole in the tissue. Handling the fastener separately from the installation tool occupies both of the medical professional's hands and can be burdensome, awkward, and difficult to maintain a grip on and accurately place the fastener. Additionally, directly manually handling the fastener can increase the likelihood of harmful germs and bacteria transferring from the medical professional to the fastener prior to insertion into the tissue, and increase the likelihood of damage to the fastener.

Commonly, surgical fasteners are temporary, and require removal after surgery or at any of various times throughout a healing process. Orthopedic fasteners can require removal at some time following surgery for various reasons. For example, a fastener embedded in bone can act as a stress riser, which may increase the risk of an undesired fracture in the bone proximate the fastener location. Additionally, over time, the position of a fastener can shift away from the initial embedded position, which may result in an infection or other negative side effect. At the very least, an un-removed fastener may simply cause discomfort, such as by conducting cold temperatures, or creating pain and irritation in the tissue surrounding the fastener. Although less likely, an un-removed fastener may result in the potential inconvenience associated with metal detector false alarms. In addition to potentially negative consequences caused by leaving hardware fixed in a patient's bone, some negative effects may be caused during the installation of the hardware. For example, a fastener may become damaged during the process of insertion, such as stripping the head or breaking the head off entirely. Such damage to the head can make further insertion and/or extraction of the fastener highly problematic.

The nature of bone itself also presents some challenges to removing a temporary fastener. As the bone heals, it tends to encase the fastener more tightly, which can increase the torque required to loosen the fastener from the bone. The bone may also encroach upon the head of the fastener making it difficult to access. Another problem arises from the hollow nature of bones. When removing a screw, once the threaded portion has been unscrewed from the distal cortex of the bone, there may be insufficient resistance offered by the screw head to keep the installation tool engaged. Moreover, even if the screw can be extracted to the point where the proximal end of the threaded portion comes into contact with the proximal cortex of the bone, the bone may have grown tightly around the shank, which can impede further progress. Accordingly, when removing a fastener, there may be insufficient resistance to keep the installation tool engaged in the head for the threads to bite.

Some conventional fasteners employ various head and installation tool receptacle designs in an attempt to improve the coupling between the fastener and installation tool, which can improve the process of installing and removing fastener. However, such conventional fasteners often fail to provide adequate coupling between the fastener and installation tool for both installation and removal of a fastener, particularly where one-handed operation in medical and surgical applications is desired. Some systems include installation tools that secure the fastener to the installation tool prior to installation and removal in an attempt to facilitate one-handed operation. These systems, however, fail to provide adequate ease in operation and robustness necessary for many medical applications, as well as suffer from other significant shortcomings.

Additionally some conventional fasteners (e.g., bone implants) are designed for permanent placement, as opposed to temporary placement. Many of these permanent fasteners and the associated installation tools are not equipped to remove the fasteners following implantation, especially when a high-torque is necessary for removal. Moreover, these permanent fasteners and installation tools are often deficient for installing fasteners in applications requiring a high-torque for installation.

One particular conventional permanent implant described in U.S. Patent Application Publication No. 2008/0249577, filed Apr. 2, 2008, ("the '577 Publication") includes a dome-shaped (i.e., hollow hemispherical shaped) head. The hemispherical surface of the head is designed to match the contour of a load-bearing surface of a joint. The dome-shaped head has small notches about an outer periphery of the head which can be engaged by an installation tool specifically designed for use with the implant having the dome-shaped head. The installation tool includes several arms that can be actuated to engage the small notches during installation and disengage the notches when installation is complete. Because the outer surface of the implant will act as a load-bearing surface when installed, the outer surface is designed to be substantially smooth and free of irregularities. Accordingly, the notches are sized and shaped to occupy a significantly small portion of the outer surface (e.g., the outer surface area is maximized while the notch size is minimized). The arms are likewise small and flexible for engaging and disengaging the notches. Because the notches and arms are small, the permanent implant and installation tool are not sufficiently robust to handle many high-torque medical applications. Additionally, the arms are angled to enter the notches in an outer-to-inner direction such that a significant portion of the arms protrude outwardly from the outer periphery of the dome-shaped head (see FIG. 4(b) of the '577 Publication). The outwardly protruding arms would be prone to catching or disturbing tissue adjacent the implant during installation of the implant.

Other challenges analogous to those discussed above may also exist in non-medical fastener applications, such as applications involving materials (e.g., wood, metal, and plastic), or any applications where a reliable, easily operable, and secure fastener, and/or system and method for insertion and/or removal of the fastener is desired.

SUMMARY

From the foregoing discussion, it should be apparent that a need exists for an apparatus, system, and method for the installation and removal of surgical fasteners that promotes a secure engagement between an installation tool and the fasteners. Beneficially, such an apparatus, system, and method would also be useful in non-medical applications. The present subject matter has been developed in response to the present state of the art, and in particular, in response to the problems and needs in the art that have not yet been fully solved by currently available installation tools and fasteners. Accordingly, the present subject matter has been developed to provide an apparatus, system, and method for installing and removing a fastener, which overcome at least one, many, or all of the above-discussed shortcomings in the art.

According to one embodiment, a fastener includes a shank defined about a central axis and a head coupled to the shank. The head includes a continuous receptacle circumscribing the central axis. The continuous receptacle includes a radially inner surface that is angled radially inwardly toward the central axis in a head-to-shank direction.

In some implementations, the continuous receptacle has an annular shape. In certain implementations, the continuous receptacle includes a radially outer surface angled radially inwardly toward the central axis in the head-to-shank direction. The continuous receptacle can be located on the head between the central axis and an outer periphery of the head. According to some implementations, the continuous receptacle includes an opening defined between a first circular edge formed in the head and a second circular edge formed in the head. The first and second circular edges can define concentric circles.

In another embodiment, a fastener and installation tool system includes an installation tool and a fastener similar to the fastener of the above-mentioned apparatus. The installation tool includes a flexible collet and a collet flexing portion. The flexible collet includes a proximal end and a distal end. The distal end includes a plurality of projections each matingly engageable with the continuous receptacle. The collet flexing portion is engageable with the collet to flex the collet and draw the plurality of projections radially inward toward each other.

According to some implementations, the continuous receptacle has an annular shape and the plurality of projections each has an arcuate shape. When radially inwardly drawn toward each other, the plurality of projections can collectively define an annular shape corresponding to the annular shape of the continuous receptacle.

In certain implementations, the fastener includes a central bore that extends through the shank and head. Further, the flexible collet includes an alignment rod that is engageable with the central bore to align the fastener and the flexible collet.

According to certain implementations, the plurality of projections are matingly engageable with the continuous receptacle independently of the relative rotational orientation of the continuous fastener and flexible collet. The plurality of projections can be positioned about a periphery of the proximal end of the flexible collet. Further, each of the projections can include a radially inner surface that extends radially outwardly in a direction away from the distal end of the collet toward the proximal end of the collet.

According to yet another embodiment, a fastener includes a shank concentrically aligned with a central axis of the fastener. The fastener also includes a head coupled to the shank. The head extends from a proximal end to a distal end and the shank extends from a proximal end adjacent the distal end of the head to a distal end away from the distal end of the head. The head includes at least one receptacle spaced radially outwardly away from the central axis of the fastener. A radially innermost portion of the at least one receptacle extends radially inwardly toward the central axis in a direction away from the proximal end of the head.

The at least one receptacle can be an annular-shaped receptacle in certain implementations. In some implementations, the at least one receptacle circumscribes the central axis. The radially innermost portion of the at least one receptacle can form a minor angle with the central axis of the fastener of at least 5°. In certain implementations, the radially innermost portion of the at least one receptacle forms a minor angle with the central axis of the fastener of at least 10°. Similarly, an outermost portion of the at least one receptacle can form a minor angle with the central axis of the fastener of at least 10°.

According to some implementations, the at least one receptacle is spaced radially inward from an outer periphery of the head where the outer periphery is defined along a plane perpendicular to the central axis. In certain implementations, the at least one receptacle has a substantially triangular-shaped cross-section defined along a plane parallel to the central axis of the fastener.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the features, advantages, and characteristics of the apparatus, system, and method described herein may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments of the subject matter.

These features and advantages of the present subject matter will become more fully apparent from the following description and appended claims, or may be learned by the practice of the subject matter as set forth hereinafter.

BRIEF DESCRIPTION OF THE DRAWINGS

In order that the advantages of the subject matter will be readily understood, a more particular description of the subject matter briefly described above will be rendered by reference to specific embodiments that are illustrated in the appended drawings. Understanding that these drawings depict only certain illustrative embodiments and are not therefore to be considered to be limiting of its scope, further embodiments of the subject matter will be described and explained with additional specificity and detail through the use of the specification, claims, and accompanying drawings, in which:

DETAILED DESCRIPTION

Reference throughout this specification to "one embodiment," "an embodiment," or similar language means that a particular feature, structure, or characteristic described in connection with the embodiment is included in at least one embodiment of the present disclosure. Thus, appearances of the phrases "in one embodiment," "in an embodiment," and similar language throughout this specification may, but do not necessarily, all refer to the same embodiment. Furthermore, the described features, structures, or characteristics of the invention may be combined in any suitable manner in one or more embodiments. Additionally, one skilled in the relevant art will recognize that the subject matter of the present disclosure may be practiced without one or more of the specific details described herein, or with other methods, components, materials, and so forth. In other instances, well-known structures, materials, or operations are not shown or described in detail to avoid obscuring aspects of the subject matter of the present disclosure.

Figure 1:
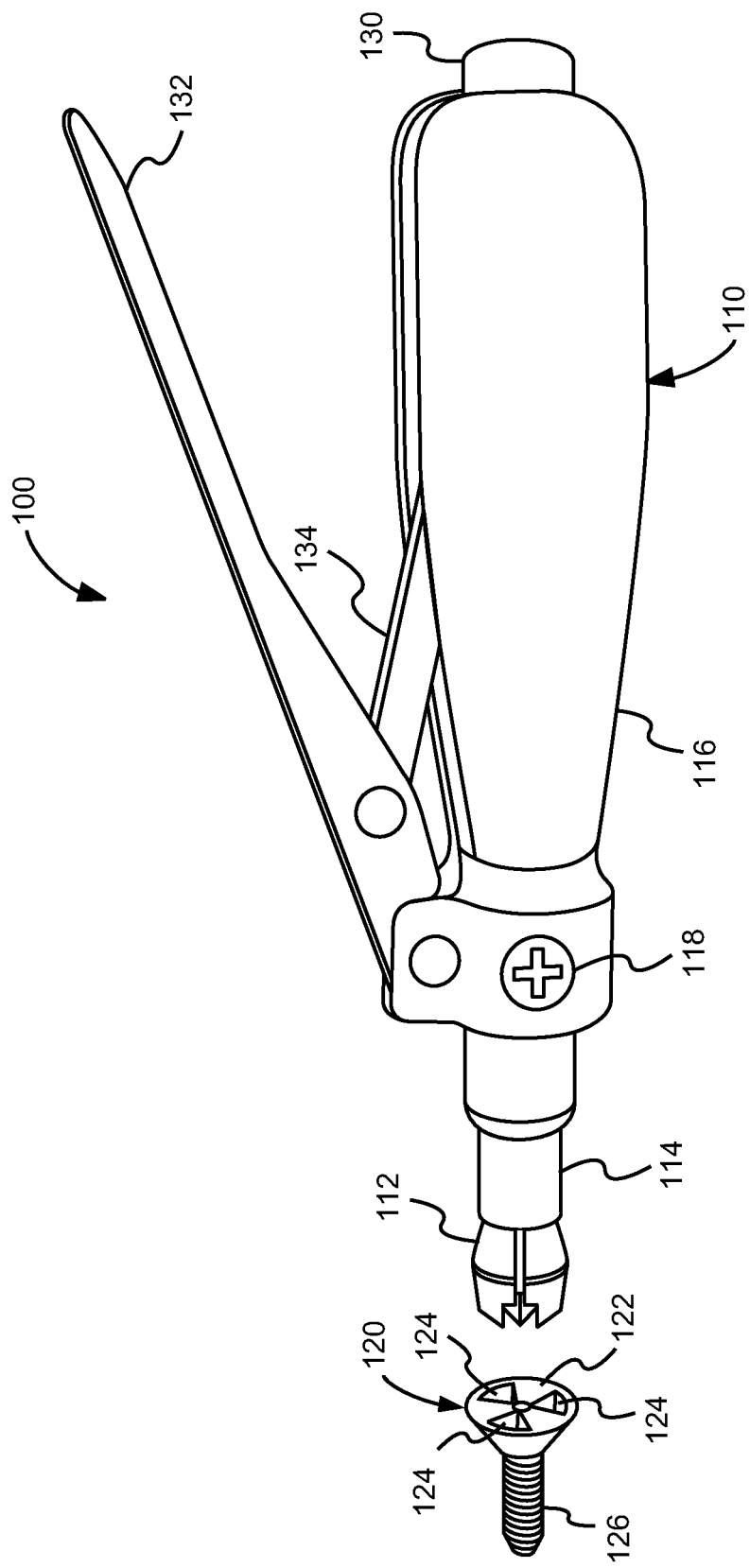
FIG. 1 is a perspective view of a fastener and installation tool system according to one embodiment.

Referring to FIG. 1, a fastener and installation tool system 100 includes an installation tool 110 and a fastener 120. The installation tool 110 is operable to secure the fastener 120 for installation of an uninstalled fastener and removal of an installed fastener. Once installed or uninstalled, the installation tool 110 is operable to unsecure the fastener 120. Generally, the installation tool 110 secures and unsecures the fastener 120 via engagement and disengagement between radially inward directed receptacles on the head of the fastener and corresponding projections on the installation tool. Engagement between the receptacles and corresponding projections allows a practitioner to install the fastener in a one-handed operation without manually contacting the fastener.

In the illustrated embodiment, the fastener 120 includes a head 122 coupled to a shank 126. The head 122 is configured to receive a mating portion of the installation tool 110. The shank 126 includes external threads 174. The external threads 174 engage tissue when installed to promote retention and prevent pull-out of the fastener after installation of the fastener in the tissue. In alternative embodiments, the shank 126 does not include threads. The fastener 120 can be used for surgical and non-surgical applications.

Figure 3:
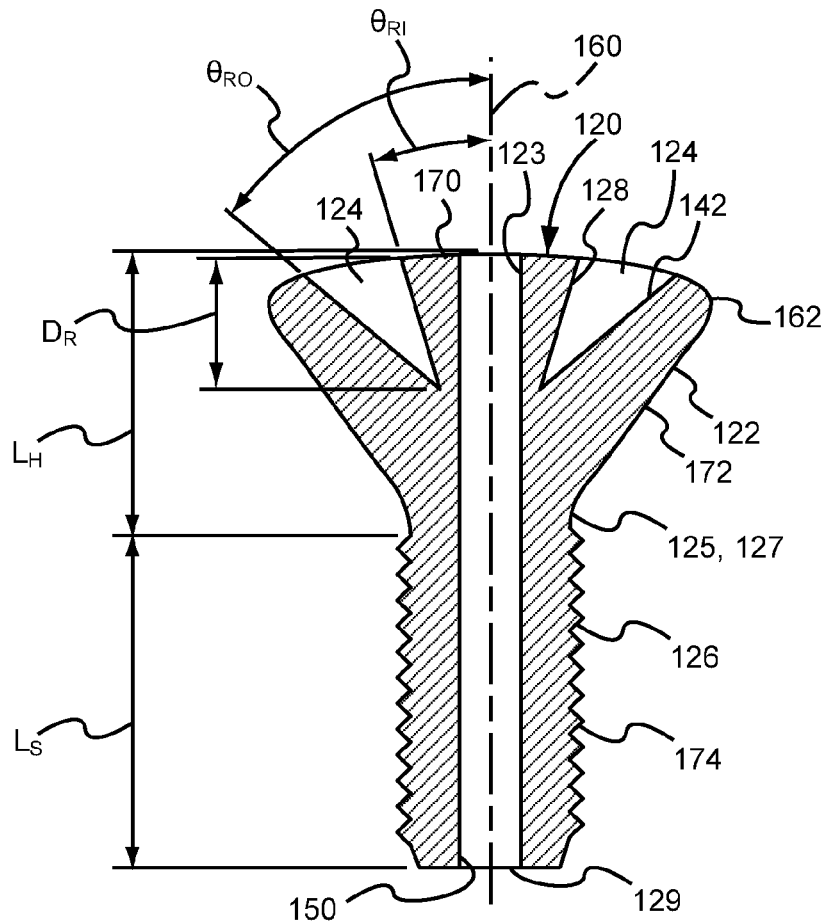
FIG. 3 is a cross-sectional side view of the fastener of FIG. 2 taken along the line 2-2 of FIG. 2.

Generally, the head 122 is defined as the relatively wide portion of the fastener 120 and the shank 126 is defined as the relatively slender portion of the fastener. More specifically, the head 122 extends from a proximal end 123 (e.g., top) to a distal end 125 (e.g., bottom). The shank 126 extends from a proximal end 127 (e.g., top) adjacent the distal end 125 of the head 122 to a distal end 129 (e.g., bottom). In the illustrated implementation, the proximal end 127 of the shank 126 is coextensive (e.g., contiguous) with the distal end 125 of the head 122. As shown, the proximal end 123 of the head 122 defines the proximal extent or boundary of the fastener 120, and the distal end 129 of the shank 126 defines the distal extent of boundary of the fastener. Similarly, the distal end 125 of the head 122 defines the distal extent or boundary of the head, and the proximal end 127 of the shank 126 defines the proximal extent or boundary of the shank. As shown in FIG. 3, the total length of the fastener 120 is equal to a length $L_H$ of the head 122 (i.e., the distance between the proximal and distal ends 123, 125 of the head) plus a length $L_S$ of the shank 126 (i.e., the distance between the proximal and distal ends 127, 129 of the shank).

Preferably, the head 122 and shank 126 each have a substantially circular-shaped cross-section along planes perpendicular to a central axis 160 of the fastener 120. However, in some embodiments, the head 122 and shank 126 have non-circular shaped cross-sections. In certain implementations, the shank 126 has a constant diameter along a length of the shank that is less than a maximum diameter of the head 122. In certain implementations, the shank 126 is defined as distal portion of the fastener 120 having a substantially constant cross-sectional area (not including threads) and the head 122 is defined as a proximal portion of the fastener having changing or variable cross-sectional areas. In some implementations, the distal extent of the head 122 has the same diameter as the proximal extent of the shank.

Further, as shown, the head 122 is substantially solid (e.g., non-hollow or non-dome shaped). More specifically, the head 122 has a maximum wall thickness along a plane perpendicular to the central axis 160 that is substantially equal to a maximum radial dimension $R_H$ of an outermost periphery 162 of the head (see FIG. 2). Additionally, the head 122 has a maximum wall thickness along a plane parallel to the central axis 160 that is substantially equal to the length $L_H$ of the head.

Figure 2:
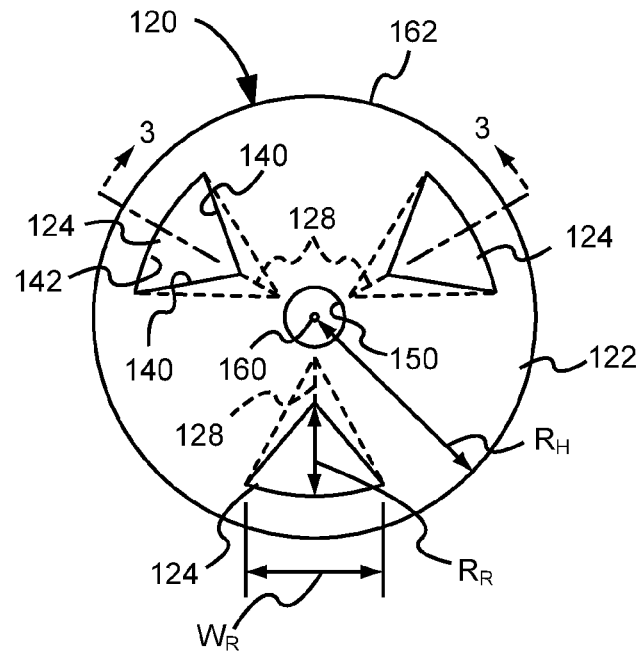
FIG. 2 is a top view of a fastener according to one embodiment.

Referring to FIGS. 2 and 3, the head 122 includes a plurality of receptacles 124 or pockets spaced-apart about the head. In the illustrated embodiment, the receptacles 124 are spaced an equal distance apart from each other and the same radial distance away from the central axis 160 of the fastener 120. However, in other embodiments, the receptacles are not spaced an equal distance apart from each other and the same radial distance away from the central axis 160. Generally, the receptacles 124 are configured (e.g., sized, shaped, and positioned) to provide a robust engagement between the projections of the installation tool 110 and the receptacles, as well as to provide a relatively large drive area to adequately distribute the torque load transferred to the fastener 120 by the installation tool 110 during installation or removal. Further, although the illustrated embodiment of the fastener 120 includes three receptacles 124, in other embodiments, the fastener 120 includes two or more than three receptacles.

The receptacles 124 each have a depth $D_R$ defined as the distance along a plane parallel to the central axis 160 between a proximal end of the receptacle and a distal end of the receptacle. Generally, the receptacles 124 extend along a substantial portion of the length $L_H$ of the head 122. For example, in some embodiments, each receptacle 124 has a depth $D_R$ that is at least between about 20% and 90% of the length $L_H$ of the head 122. In one specific implementation, each receptacle 124 has a depth $D_R$ that is at least 50% of the length $L_H$ of the head 122. In certain implementations, the depth $D_R$ may be less than 50% to reduce manufacturing complexity. In some embodiments, the depth $D_R$ is only large enough to ensure sufficient control of the fastener and torque transfer from the installation tool to the fastener.

Each receptacle 124 includes a radially innermost surface or edge 128, a radially outermost surface or edge 142, and at least two side surfaces 140 extending between the radially innermost and outermost surfaces or edges. The radially innermost surface or edge 128, radially outermost surface or edge 142, and at least two side surfaces 140 define an opening of the receptacle 124 formed in a proximal surface 170 of the fastener. In certain embodiments, the combined area of the openings of the receptacles 124 is between about 10% and about 70% of the area of the proximal surface 170 to provide a robust engagement between the projections of the installation tool 110 and the receptacles. In one particular embodiment, the combined area of the openings is at least about 40% of the area of the proximal surface 170.

In the illustrated embodiment, each receptacle 124 has a substantially triangular-shaped or delta-shaped cross-section along a plane perpendicular to the central axis 160. Accordingly, in the illustrated embodiment, each receptacle has an innermost edge 128 defined at a vertex of the receptacle. For non-triangular shaped receptacles or inverted triangular-shaped receptacles, the receptacles each can have an innermost surface 128 instead of an edge. The radially innermost edge 142 extends from the proximal surface 170 of the head 122 to a location between the proximal surface 170 and the distal end 125 of the head. The radially innermost edge 142 of each receptacle 124 is radially inwardly angled with respect to the central axis 160. More specifically, in a proximal-to-distal direction, each innermost edge 142 angles radially inwardly toward the central axis 160. Put another way, as the innermost edge 142 extends from the proximal surface 170 to the distal end of the receptacle 124, the edge converges toward the central axis 160.

As shown in FIG. 3, each innermost edge 142 is radially inwardly angled to define a minor angle $\theta_{RI}$ with respect to the central axis 160. Preferably, the receptacles 124 are configured such that the minor angle $\theta_{RI}$ is large enough to retain the projections of the installation tool 110 within the receptacles 124 during installation of the fastener 120, but small enough to reduce the articulation of the installation tool necessary to secure the fastener (as will be described in more detail below). In some implementations, for example, the minor angle $\theta_{RI}$ is between about 5° and about 20°. In one specific implementation, the minor angle $\theta_{RI}$ is about 10°. In a manner similar to the innermost edge, the side edges 140 of each receptacle 124 can also be angled to correspond with the angle of the innermost edge. More specifically, the side edges 140 can be angled such that the side edges diverge away from each other in a proximal-to-distal direction.

The radially outermost surface or edge 142 can be inwardly radially angled with respect to the central axis 160 in a manner similar to the radially innermost edge 128. In the illustrated embodiment, each receptacle 124 includes a radially outermost surface 142. For non-triangular shaped receptacles or inverted triangular-shaped receptacles, the receptacles each can have an outermost edge 142 instead of a surface. The outermost surface 142 defines a minor angle $\theta_{RO}$ with respect to the central axis 160. The outermost surface 142 is also inwardly angled (e.g., at a selected minor angle $\theta_{RO}$) to facilitate initial engagement between the projections of the installation tool 110 and the receptacles, as well as to promote a more consistent (e.g., uniform) side wall thickness of the fastener 120. In some implementations, for example, the minor angle $\theta_{RO}$ is between about 30° and about 80°. In one specific implementation, the minor angle $\theta_{RO}$ is about 60°. Although the illustrated embodiment includes an inwardly radially angled outermost surface 142, in other embodiments, the outermost surface 142 of each receptacle 124 is not inwardly angled. For example, in some embodiments, the radially outermost surface 142 is substantially parallel to the central axis 160 of the fastener 120.

Referring back to FIG. 2, the receptacles 124 each have a maximum radial dimension $R_R$ extending between the innermost edge 128 and outermost surface 142. Generally, the receptacles 124 extend radially along a substantial portion of the proximal surface 170 of the head 122 to provide a robust engagement between the projections of the installation tool 110 and the receptacles, as well as to facilitate ease in mating the projections with the receptacles. In some embodiments, for example, each receptacle 124 has a maximum radial dimension $R_R$ that is at least between about 20% and 80% of the maximum radial dimension $R_H$ of the outermost periphery 162 of the head. In one specific embodiment, the maximum radial dimension $R_R$ is at least 50% of the maximum radial dimension $R_H$. In certain implementations, such as for fasteners having a relatively small size, the maximum radial dimension $R_H$ extends from the innermost edge 128 radially outwardly to the outermost periphery 162 of the head.

Additionally, as shown in FIG. 2, the receptacles 124 each have a maximum width $W_R$. Generally, the receptacles 124 extend circumferentially along a substantial portion of the proximal surface 170 of the head 122 to provide a robust engagement between the projections of the installation tool 110 and the receptacles, as well as to facilitate ease in mating the projections with the receptacles. In some embodiments, for example, each receptacle 124 has a maximum width $W_R$ that is at least between about 5% and 25% of the circumference of the outermost periphery 162 of the head. In one specific embodiment, the maximum radial dimension $R_R$ is at least 10% of the circumference of the outermost periphery 162.

The fastener 120 includes a central bore 150 extending an entire length of the fastener coaxially with the central axis 160. The central bore 150 can be used in conjunction with a cannulated fastener system including a guide wire. More specifically, proper placement and installation of the fastener 120 into bone tissue can be facilitated by positioning a guide wire within the central bore 150 and utilizing the guide wire as a guide. Although the illustrated embodiment includes a central bore 150, in other embodiments, the fastener 120 does not include a central bore.

The head 122 of the fastener 120 can have any of various shapes. In the illustrated embodiment, as discussed above, the head has a generally circular-shaped cross-section along a plane perpendicular to the central axis 160. However, in other embodiments, the cross-section of the head 122 along a plane perpendicular to the central axis 160 is differently shaped, such as, but not limited to, triangular, ovular, polygonal, and the like. The head 122 also has a generally triangular-shaped cross-section along a plane parallel to the central axis 160 somewhat similar to head shape of a conventional flat head or oval head screw. More specifically, although slightly convex, the proximal surface 170 of the head 122 is substantially perpendicular to the central axis and a distal surface 172 of the head converges toward the central axis 160 in a proximal-to-distal direction. In some embodiments, the proximal surface 170 is one of a convex, concave, and flat surface. In yet some embodiments, the distal surface 172 is at least one of a convex, concave, and flat surface (i.e., a surface substantially perpendicular to the central axis 160 similar to a conventional round head or PAN head screw). Alternatively, cross-sectional shape of the head 122 along a plane parallel to the central axis 160 can be a shape other than triangular, such as, for example, circular, or poly-circular, such that the overall shape of the head can be spherical or poly-spherical.

In alternative embodiments, the fastener and installation tool system 100 is configured to install and remove fasteners having configurations different than the fastener 120. For example, referring to FIGS. 4 and 5, the system 100 can be used with a fastener 220 that includes a head 222 coupled to a shank 226. Like the head 122 of the fastener 120, the head 222 is configured to receive a mating portion of the installation tool 110. More specifically, the head 222 includes a plurality of receptacles 224 having a size and shape similar to the receptacles 124 of head 122. However, unlike head 122, with the receptacles 124 spaced radially inward of the outer periphery 162, the head 222 includes receptacles 224 positioned on and about an outer periphery 229 of the head.

Similar to the receptacles 124 of the fastener 120, the receptacles 224 of the fastener 220 each include a radially innermost edge 228 that is angled with respect to a central axis 260 of the fastener 220, as well as angled side surfaces 240 extending radially outward therefrom. But, the receptacles 224 do not include a radially outermost surface or edge formed in the head 222 such that the outer periphery 229 of the head effectively includes the innermost edges 228 and side surfaces 240 of the receptacles. In certain embodiments, the fastener 220 also includes a central bore 250 coaxial with the central axis 260.

The radially innermost edges 228 each define a minor angle $\theta_{RI}$ with respect to the central axis 160. Further, each receptacle 224 has a maximum radial dimension $R_R$ extending between the innermost edge 228 and an imaginary extension 242 of the circular outer periphery 229 of the head 222. The receptacles 224 each include a maximum width $W_R$ and a depth $D_R$ similar to the maximum width and depth of the receptacles 124. The maximum width $W_R$ and a depth $D_R$ of the receptacles 224 can have sizes relative to the size of the head 222 similar to the receptacles 124 and head 122 except that in some embodiments, the depth $D_R$ of the receptacles 224 can be the same as the length $L_H$ of the head 222.

Referring back to FIG. 1, the installation tool 110 is similar to the positional fixation instrument described in U.S. patent application Ser. No. 12/467,175, filed May 15, 2009 (hereinafter the '175 Application), which is incorporated herein by reference. More specifically, the installation tool 110 includes a removable collet 112 or chuck tip for securing the fastener 120. The collet 112 is initially tightened by adjusting a tightening portion of the installation tool 110 and further tightened (e.g., locked in place) by adjusting a locking portion of the installation tool.

The tightening portion is adjusted via actuation of a knob 130. More specifically, the tightening portion is adjusted by turning the knob 130 in one direction, typically clockwise, to draw the collet 112 into a chuck body 114. The collet 112 may be opened and loosened by turning the knob 130 in an opposite direction, which moves the collet 112 away from the chuck body 114.

The locking portion of the installation tool 100 includes a lever 132 and locking member 134. The collet 112 may be further tightened and locked by depressing the lever 132 relative to a handle 116, which causes the locking member 134 to descend into a channel 136 formed within a side of the handle 116. In contrast, the collet 112 may be unlocked by lifting the lever 132 relative to the handle 116. In some implementations, when fully depressed, the lever 132 fits within a channel 136 of the handle 116 to provide an ergonomic handhold for operation of the installation tool 100.

Figure 6:
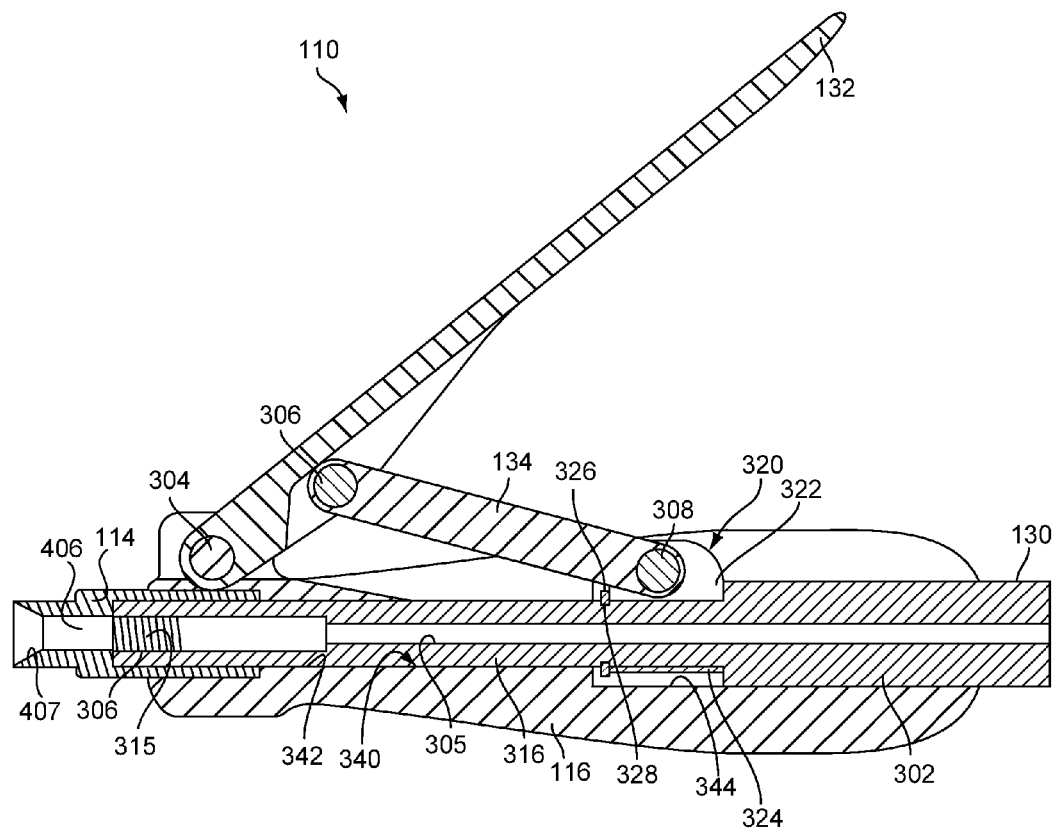
FIG. 6 is a cross-sectional side view of an installation tool according to one embodiment shown in an unlocked position.

The handle 116 is roughly cylindrical in shape, with the lever 132 being mounted to a top of the handle (as shown in FIG. 6). In alternative embodiments, the handle can have any of various shapes, such as ovular, triangular, elliptical, and hexagonal. The installation tool 110 includes a chuck seat 303 countersunk into the handle 116 (see FIG. 7). The chuck seat 303 matingly receives the chuck body 114 as the chuck body encircles a central shaft 316 of the installation tool 110 (see FIG. 6). The shaft includes a threaded portion 315 that accepts a threaded proximal end 500 of the collet 112. A central bore 305 runs the length of the tool 110 to allow passage of a guide wire (not shown) as used in conjunction with a cannulated fastener. The bore 305 is collectively defines by the combination of bores extending through the collet 112, chuck body 114, shaft 316, and knob 130.

Figure 9:
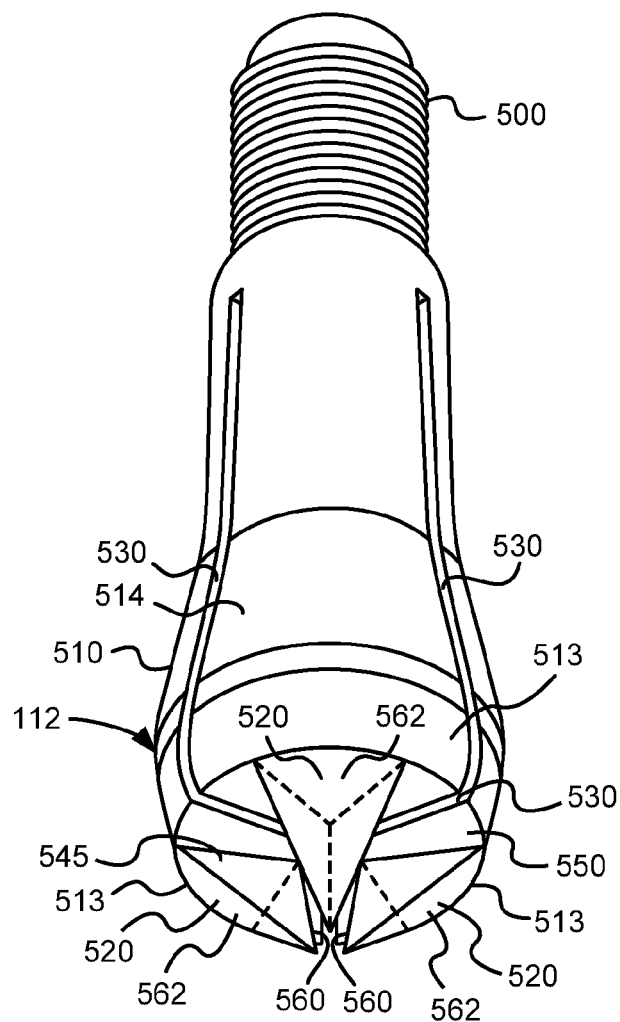
FIG. 9 is a perspective frontal view of a collet of an installation tool according to one embodiment.
Figure 10:
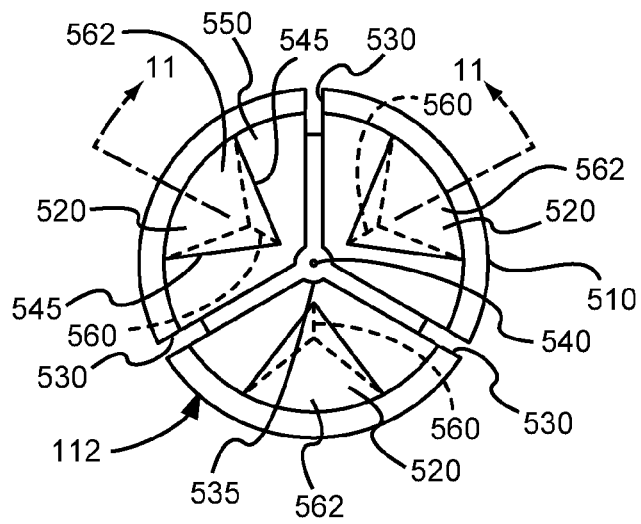
FIG. 10 is a top view of the collet of FIG. 9.

Referring to FIG. 9, the collet 112 has a threaded end portion 500 and a compressible end portion 510 generally opposite the threaded end. The threaded end portion 500 is threadably engageable with a threaded portion of an internal rod co-rotatably coupled to the knob 130 such that rotation of the knob correspondingly rotates the rod. The compressible end portion 510 is resiliently compressible to secure the fastener 120 and decompressible to release the fastener 120.

The collet 112 is configured to secure the fastener 120 by engaging the receptacles 124 about the proximal surface 170 of the head 122. To facilitate engagement between the collet 112 and receptacles 124, the collet 112 includes a plurality of projections or teeth 520 spaced-about the compressible distal end portion 510 of the collet. The compressible distal end portion 510 include a plurality of sections 513 each movable relative to each other. The sections 513 are defined between two adjacent longitudinal slits 530 such that each section 513 is separated from an adjacent section 513 by a respective one of the slits 530. The longitudinal slits 530 each extend radially from a central bore 535 extending coaxially with a central axis 540 of the collet 112 to an outer surface of the collet 112. Each section 513 is radially inwardly flexible toward the central axis 540 (and the other sections) about a flex point adjacent a distal end of the slits 530 upon receipt of a radially inwardly directed force sufficient to overcome a bias of the flex point (see, e.g., FIG. 11). Similarly, each section 513 is radially outwardly movable away from the central axis 540 upon release of the radially inwardly directed force. In certain implementations, the range of radial motion of the sections 513 is based at least on a width of the slits 530 and the thickness of the collet 112 adjacent the distal end of the slits.

The compressible distal end portion 510 of the collet 112 includes a distal end surface 550 defined as the collective distal end surfaces 550 of the sections 513. Each section 513 includes a respective projection 520 protruding distally from the distal end surface 550 of the projection. The projections 520 are sized and shaped to mateably engage a respective one of the receptacles 124. Generally, in some embodiments, the projections 520 have the same shape and size as the receptacles 124. More specifically, each projection 520 includes a radially innermost surface or edge 560 corresponding with the radially innermost surface or edge 128 of the receptacles 124. Like the innermost edge 128 of the receptacles 124, the innermost edge 560 of the projections 520 is radially inwardly angled with respect to the central axis 540. For example, in a distal-to-proximal direction, each innermost edge 560 angles radially inwardly toward the central axis 540. Preferably, a minor angle defined between the innermost edge 560 and the central axis 540 is approximately equal to the minor angle $\theta_{RO}$ between the innermost edge 128 and the central axis 160 of the fastener 120.

The projections 520 can each include a radially outermost surface or edge 562 corresponding with the radially outermost surface or edge 142. The radially outermost surface or edge 562 can be angled relative to the central axis 540. In certain embodiments, the minor angle defined between the outermost surface or edge 562 and the central axis 540 is about the same as the minor angle $\theta_{RO}$ between the outermost surface or edge 142 and the central axis 160. For receptacles 124 having side surfaces 140 angled with respect to the central axis 160, the projections can have angled side surfaces 564 corresponding to the side surfaces 140 of the receptacles.

The projections 520 are circumferentially spaced-apart from each other a distance equal to the circumferential spacing of the receptacles 124. However, as shown in solid line in FIG. 11, when the distal end portion 510 of the collet 112 is uncompressed, the radial distance of the projections 520 away from the central axis 540 of the collet is offset from (e.g., slightly greater than) the radial distance of the receptacles 124 away from the central axis 160. The radial offset compensates for the radially inward compression of the distal end portion 510 such that when the distal end portion is compressed, as shown in dashed line in FIG. 11, the radial distance of the projections 520 away from the central axis 540 is approximately the same as the radial distance of the receptacles 124 away from the central axis 160.

Figure 4:
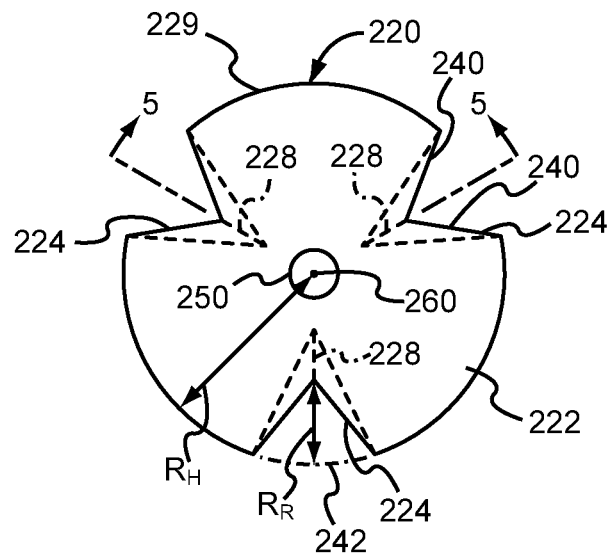
FIG. 4 is a top view of a fastener according to another embodiment.
Figure 5:
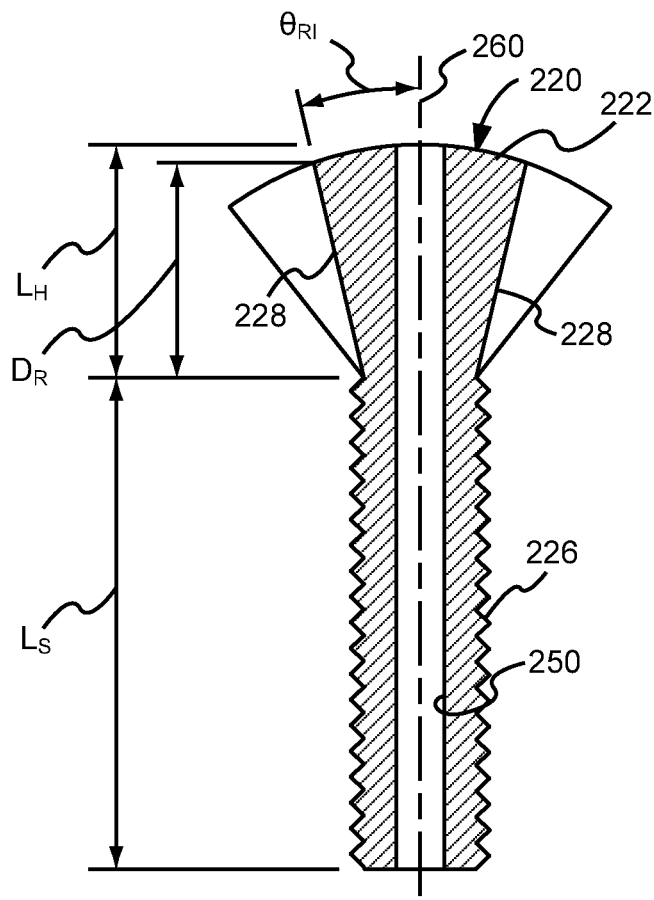
FIG. 5 is a cross-sectional side view of the fastener of FIG. 3 taken along the line 5-5 of FIG. 4.

A collet similar to the collet 112 can be used to secure the fastener 220 of FIGS. 4 and 5. For example, the projections 520 can be sized and shaped to mate with the receptacles 224. However, because the receptacles 224 are positioned on the outer periphery 229 of the head 222, the radial distance of the projections 520 away from the central axis 160 would need to be increased to accommodate the increased outwardly radial positioning of the receptacles 224 compared to the receptacles 124.

The illustrated collet 112 extends lengthwise in a direction substantially parallel to the central axis 540. In other words, the collet 112 is substantially straight. In other embodiments, such as for use in dental applications, the collet can be angled (e.g., substantially V-shaped, L-shaped, or arcuate-shaped along its length) to facilitate the installation of fasteners in spaces that are difficult to access, such as between teeth within a patient's mouth.

The collet 112 is installed by inserting its threaded proximal end 500 through the chuck body 114 into a threaded portion 315 of a shaft 316 of the installation tool 110 and screwing it firmly in place. As shown in FIG. 6, the chuck body 114 is seated in the handle 116 and held in place by a set screw 118, which extends through an aperture in the handle and engages a depression 404 in the chuck body (see FIG. 8).

As shown in FIG. 6, the knob 130 of installation tool 110 is coupled to a shaft 316 via an extension 302 of the knob 130. In the illustrated embodiment, the knob 130, shaft 316, and extension 302 form a one-piece monolithic construction with each other. The handle 116 includes a central bore 340 having a first proximal portion 342 coaxial with a second distal portion 344. The first proximal portion 342 is sized to matingly receive the shaft 316 and the second distal portion 344 is sized to matingly receive the extension 302. The shaft 316 and extension 302 are rotatable within the first proximal and second distal portions 342, 344, respectively. Preferably, the first proximal portion 342 retains the shaft is substantially coaxial alignment with the first proximal portion and the second distal portion 344 retains the extended portion is substantially coaxial alignment with the second distal portion. The lever 132 is connected to the handle 116 via a first pivot joint 304. A second pivot joint 306 connects the lever 132 to a distal end of the locking member 134. A proximal end of the locking member 134 is in turn connected to the extension 302 of the knob 110 via a third pivot joint 308.

The proximal end of the locking member 134 is secured to the third pivot joint 308 via a shackle member 320 coupled to the shaft 316. The shackle member 320 is configured to ensure that the third pivot joint 308 moves axially when the shaft 316 moves axially, and that the shaft 316 is rotatable relative to the third pivot joint. The shackle member 320 includes two space-apart tabs 322 extending vertically away from the shaft 316 and a sleeve portion 324 wrapped about at least half of the periphery of the shaft. The proximal end of the locking member 134 is positioned between the tabs 322 and secured to the tabs by extending the pivot joint 308 through apertures in the tabs and locking member.

When secured to the proximal end of the locking member 134, the shackle member 320 is configured to retain the third pivot joint 308 in a vertically fixed location (as shown in FIG. 6) relative to the shaft 316, but allow the shaft to rotate relative to the shackle member. The shackle member 320 is prevented from moving axially or horizontally (as shown in FIG. 6) relative to the shaft 316 through use of a stop 326 secured to and fixed relative to the shaft and extension 302. More specifically, the shackle member 320 is effectively sandwiched between the stop 326 and the extension 302 of the knob 130. The stop 326 prevents movement of the shackle member 320 in a first axial direction relative to the shaft 316 and the extension 302 prevents movement in a second axial direction opposite the first axial direction relative to the shaft. The stop 326 transfers collet disengaging thrust loading from the lever 132 to the shaft 316 when releasing a fastener from the collet 112 and the extension 302 transfers collet engaging thrust loading from the lever 132 to the shaft 316 when securing a fastener in the collet. In one specific embodiment, the stop 326 is an external snap ring engaged within a recess 328 formed in the outer surface of the shaft 316.

Figure 7:
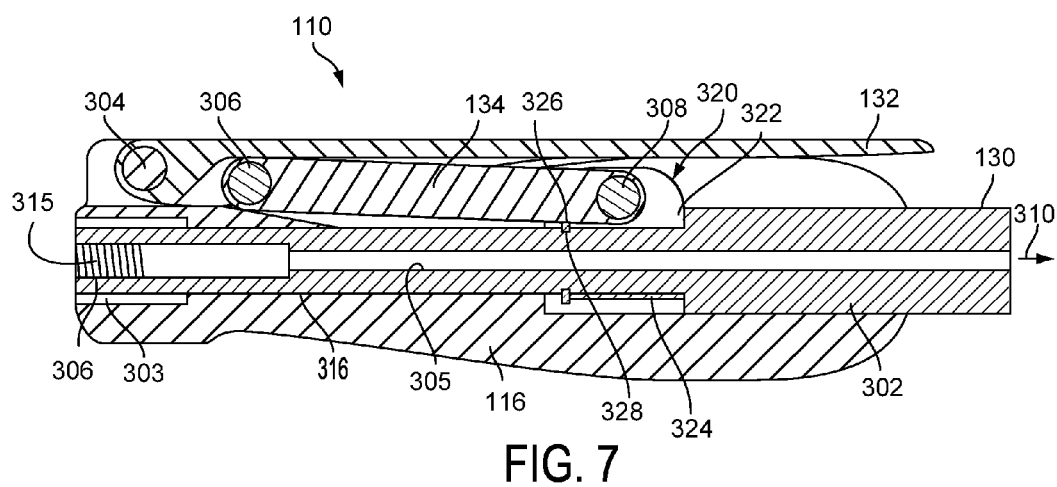
FIG. 7 is a cross-sectional side view of the installation tool of FIG. 6 shown in a locked position.

Referring to FIG. 7, as the lever 132 is depressed, the second pivot joint 306 is brought directly into line with the first and third pivot joints 304, 308 to drive the shaft 316 and knob 130 in a proximal direction, i.e., distal-to-proximal direction, as indicated by directional arrow 310. Movement of the shaft 316 and knob 130 in the proximal direction 310 after the collet 112 has been tightened against the chuck body 112 using the knob results in the application of a maximal compression force between the compressible distal end portion 510 of the collet 112 and the chuck body 114 as described above. When the lever 132 is in the fully closed position as shown, the second pivot joint 306 is substantially aligned with, but slightly below a line between, the first pivot joint 304 and third pivot joint 308, thus diverting a small amount of the maximal compression force into a downward moment of force which holds the lever 132 down and locks the closing installation tool 110 in the fully closed position. Note that the lever 132 extends proximally beyond the handle 116, providing convenient access for lifting it to unlock the installation tool 110.

Figure 8:
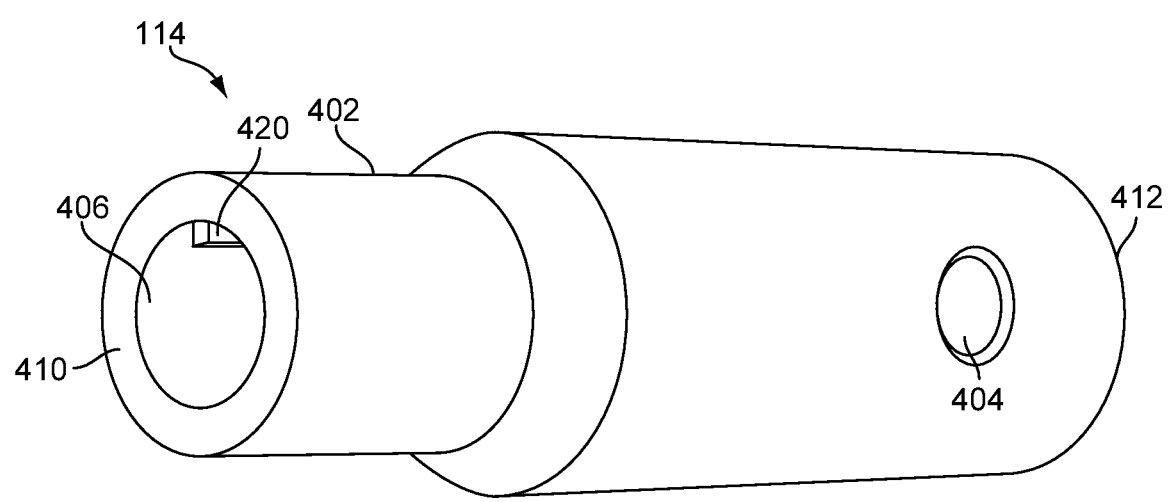
FIG. 8 is a perspective view of a chuck body according to one embodiment.

As shown in FIG. 8, a central bore 406 runs a length of the chuck body 114 from a distal end 410 to a proximal end 412. The chuck body 114 includes a collet engaging portion 402 extending from the distal end 410 to a location intermediate the distal end and proximal end 412. The central bore 406 along the collet engaging portion 402 is inwardly tapered in a distal end to proximal end direction (see, e.g., tapered surface 407 of FIG. 6). The taper of the tapered surface 407 of the central bore 806 approximately corresponds with a distal-to-proximal taper of a tapered surface 514 of the compressible distal end portion 510 of the collet 112 in an uncompressed state (see FIG. 9). When initially assembled, the corresponding tapered surfaces 407, 514 of the central bore 406 and distal end 512 of the collet 112 engage each other such that the distal end 510 of the collet 112 matingly seats within the central bore.

As the lever 132 is closed, the compressible distal end portion 510 of the collet slides along the central bore 406 of the collet engaging portion 402 in the distal-to-proximal direction relative to the central bore such that the wall of the central bore exerts an inwardly directed force against the compressible distal end portion of the collet. The inwardly directed force causes the compressible distal end portion 510 of the collet 112 to gradually flex and radially compress. The tapered nature of the engaging surfaces distributes the inwardly directed force evenly across the distal end 510 of the collet 112 to facilitate ease in compressing the distal end against the fastener 120. The tapered surface 407 of the central bore 406 is also configured to engage and facilitate compression of a distal end of a collet having a curved or arcuate shaped outer surface.

The chuck body 114 also includes a key or spline 420 extending inwardly from the inner surface of the central bore 406 in a direction parallel to the axis of the chuck body. The key 420 can extend between the distal end 410 to a location intermediate the distal end 410 and the proximal end 412. The key 420 is configured to engage a keyway or slot (not shown) formed in the collet 112 and extending in a direction parallel to the axis of the collet. In other words, as the collet 112 is inserted into the chuck body 114, the key 420 is positioned and retained within the keyway of the collet. Engagement between the key 420 and keyway reduces, restricts, or prevents rotation of the collet 112 relative to the chuck body 114. Additionally, the key 420 and keyway are axially aligned when the collet 112 is properly seated in the chuck body 114. Axial alignment between the key 420 and keyway allows for relative movement between the collet 112 and chuck body 114 in the axial or lengthwise direction. Although in the illustrated embodiments the key 420 is formed in the central bore 406 of the chuck body 114 and the keyway is formed in the collet 112, in other embodiments, the key can be formed in the collet and the keyway can be formed in the central bore.

In alternative embodiments, configurations other than a key-keyway or spline configuration can be used to reduce, restrict, or prevent relative rotation between the chuck body and collet. For example, in certain implementations, a portion of the central bore 406 can have an out-of-round cross-sectional shape and the outer surface of the collet can have an out-of-round shape at least approximately matching the out-of-round cross-sectional shape of the central bore. When the collet is inserted into the central bore 406, the out-of-round portion of the collet can be positioned within and matingly engage the out-of-round portion of the central bore 406. Because the portions of the central bore 406 and collet are out-of-round, engagement between them at least restricts rotation of the collet relative to the chuck body 114. In specific implementations, the out-of-round shape can be any of various shapes, such as hexagonal, triangular, rectangular, and ovular.

Also shown in FIG. 8 is a set screw depression 404 formed in an outer surface of the chuck body 114. The depression 404 is configured to engage the set screw 118 thereby holding the chuck body 114 firmly in place within the chuck seat 303 (see FIG. 7).

Although the illustrated embodiment depicts a specific type of installation tool 110 with a flexible collet 112, in other embodiments, other installation tools using the same or a similar flexible collet are used to secure the fastener 120. For example, in one specific embodiment, the installation tool is a power driver with an electric, magnetic, or pneumatic drill motor. The power driver can have a shaft with a flexible collet end portion and a sleeve that is movable about the flexible collet end portion to flex the end portion. The shaft and flexible collet end portion can be made of a one-piece construction, which is rotatably driven by the drill motor. The sleeve may be held in place about the flexible collet end portion by a detent mechanism. In some implementations, the detent mechanism secures the flexible collet end portion in place when the sleeve is moved and slightly rotated in one direction. Rotation of the sleeve in the opposite direction may release the detent mechanism to allow the sleeve to move out of engagement with the flexible collet end portion, resulting in the end portion returning to an unflexed state. In other embodiments, the installation tool can be a manually driven installation tool similar to the installation tool 110, but with a ratcheting mechanism that is operable to flex the collet and secure the fastener.

The components of the system 100 can be made from any of various materials. For example, in some embodiments, each of the components is made from a metal or metal alloy, such as steel, stainless steel, and/or aluminum. Also, one or more components can be made from a high-strength plastic or polymer.

Figure 11:
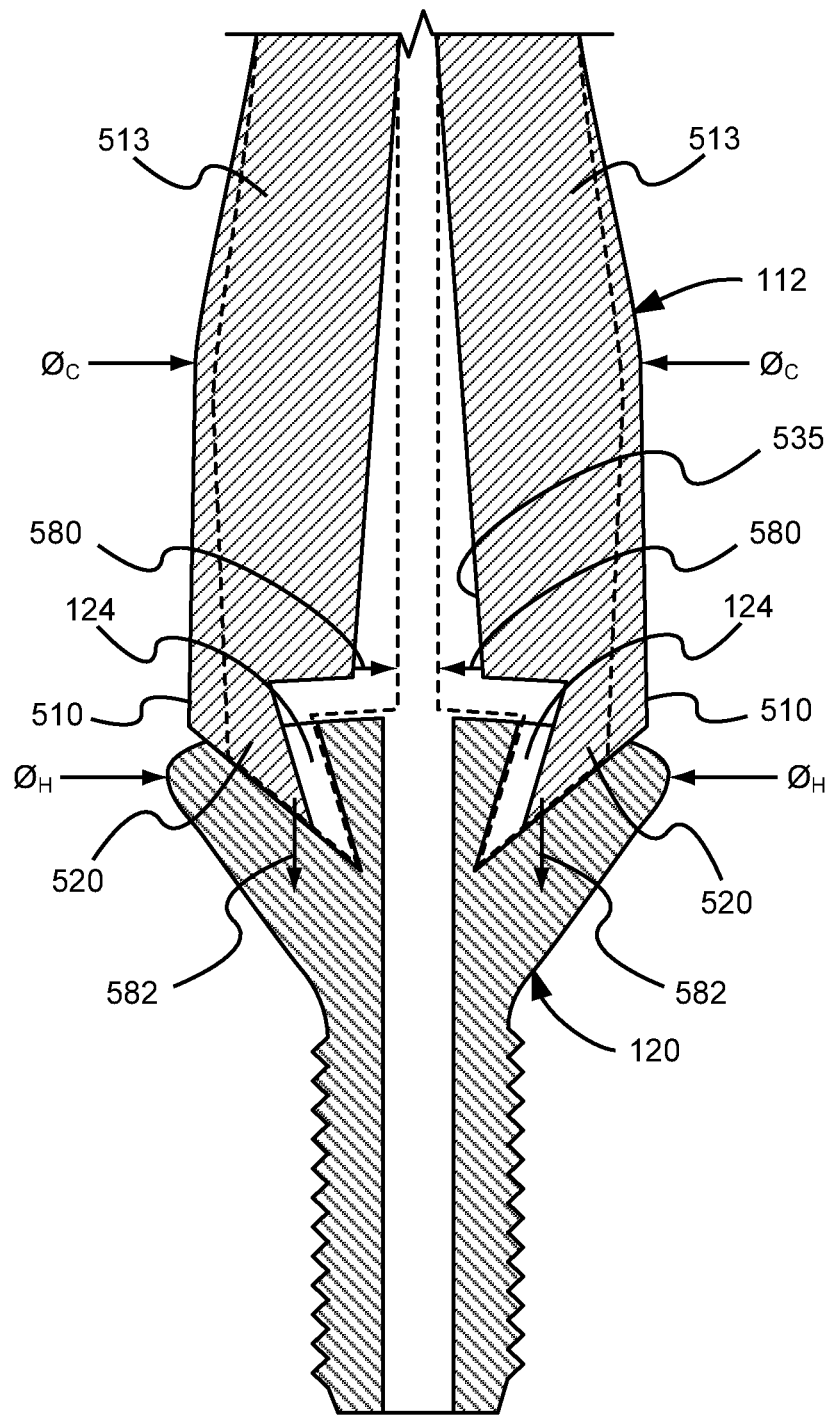
FIG. 11 is a cross-sectional side view of one embodiment of a collet of an installation tool in a first non-engaged position relative to a fastener of one embodiment, and a second engaged position relative to the fastener.

Referring to FIG. 11, the fastener 120 is secured to the installation tool 110 by positioning the projections 520 of the collet 112 in an uncompressed state at least partially within corresponding receptacles 124 of the fastener. The projections 520 are insertable into the receptacles 124 in a proximal-to-distal direction (e.g., a direction substantially parallel to the central axis 160 of the fastener 120). In other words, at least in some embodiments, the projections 520 need not be positioned radially outward of the outer periphery 162 of the fastener 120 and moved radially inwardly for insertion of the projections within the receptacles. As shown, with the collet 112 in the uncompressed state, the distance between the innermost edge 560 of the projections 520 and the central axis 540 of the collet is greater than the distance between the innermost edge 128 of the receptacles 124 and the central axis 160 of the fastener 120. Accordingly, there is sufficient clearance between the projections 520 of the collet 112 and the innermost edge 128 of the receptacles 124 to allow the projections to be at least partially positioned within the receptacles without interference.

After positioning the projections 520 at least partially within corresponding receptacles 124, the sections 513 of the compressible distal end portion 510 are compressed inwardly toward each other (as indicated by directional arrows 580) by adjusting the tightening portion of the installation tool 110 (e.g., by turning the knob 130 in a tightening direction). As discussed above, adjusting the tightening portion in this manner urges the tapered surface 514 of the compressible distal end portion 510 of the collet 112 against the chuck body 114, which causes the distal end portion to compress. As the compressible distal end portion 510 compresses, engagement between the surfaces and/or edges of the receptacles 124 and projections 520 urges the fastener 120 toward the collet 112 (as indicated by directional arrows 582) such that the projections are positioned more fully within the receptacles as indicated in dashed lines in FIG. 11.

After the compressible distal end portion 510 is initially compressed using the tightening portion of the installation tool 110, the compressible distal end portion is further compressed and locked in place by adjusting the locking portion of the installation tool (e.g., by depressing the lever 112). Eventually, between adjustment of the tightening and locking portions, the compressible distal end portion 510 of the collet 112 is sufficiently compressed that the innermost edges 560 of the projections 520 apply a radially inward directed force against the innermost edges 124 of the receptacles (and/or the side surfaces 545 of the projections apply a pressure against the side surfaces 140 of the receptacles) to secure the fastener 120 to the installation tool 110. Because of the radially inwardly angled nature of the innermost edges 124, 560 (and side surfaces 140, 545 in some embodiments) of the receptacles 124 and projections 520, respectively, the fastener 120 is prevented from disengagement with the collet 112 while the collet 112 is sufficiently compressed.

Further, as shown in FIG. 11, in some embodiments, the distal end portion 510 of the collet 112 is streamlined to reduce interference with objects or tissue adjacent the fastener installation site. More specifically, a maximum diameter $\emptyset_C$ of the collet 112 is less than a maximum diameter $\emptyset_C$ of the head 122 of the fastener 120. Accordingly, when the fastener 120 is secured to the installation tool 110 for installation or removal of the fastener, no portion of the collet 112 extends radially outward away from the outer periphery of the fastener. In this manner, the installation tool 110 does not limit the size of space within which the fastener 120 is installable (or from which the fastener is removable) and is less prone to catching on adjacent objects or tissue during installation and removal of the fastener.

The above operations can be performed to secure the fastener 120 to the installation tool 110 for installation of the fastener into a target object (e.g., bone tissue) or to remove an installed fastener from the target object.

Further, although the illustrated embodiments include a fastener with a plurality of receptacles and an installation tool with a corresponding plurality of projections, in other embodiments, the fastener can include the plurality of projections and the installation tool can include the corresponding plurality of receptacles without departing from the essence of the present subject matter.

Figure 12:
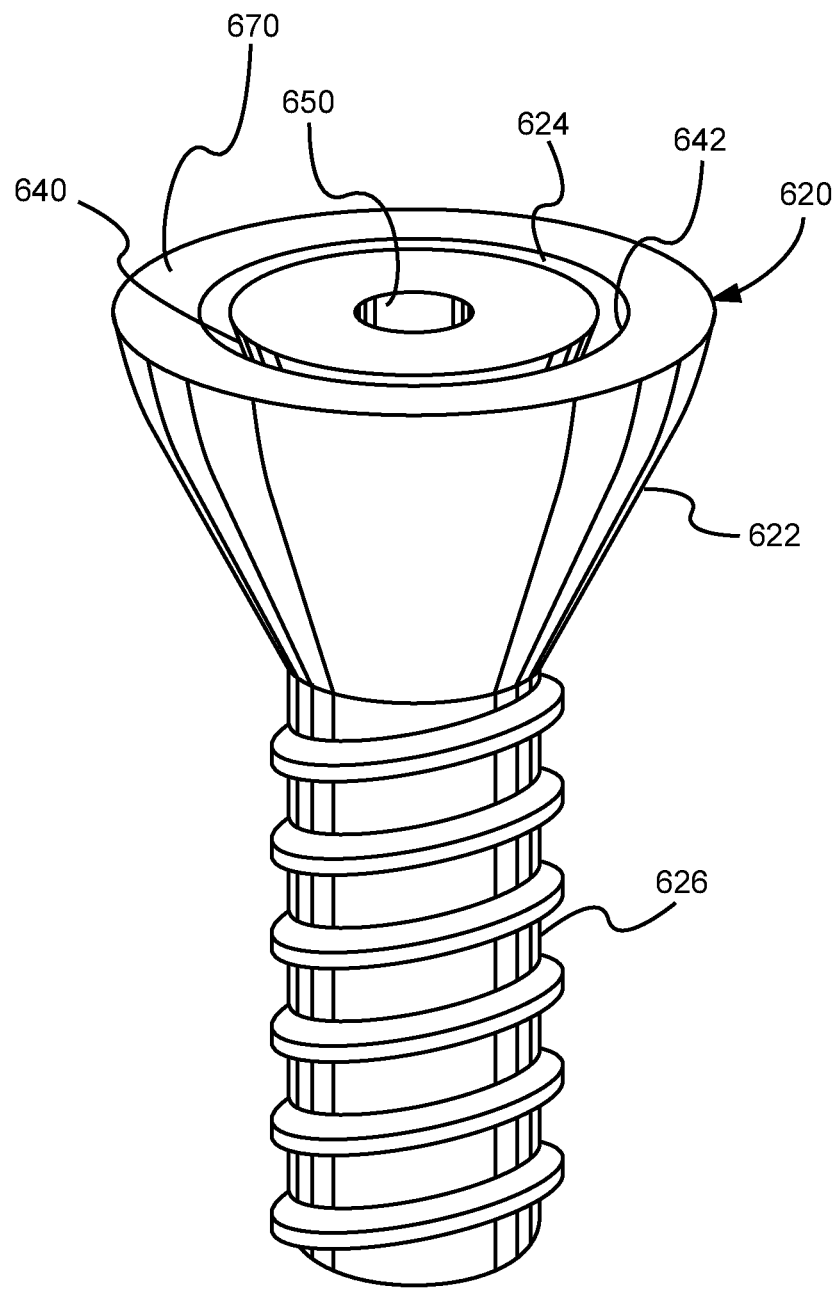
FIG. 12 is a perspective view of a fastener having an annular receptacle according to another embodiment.

According to another embodiment shown in FIG. 12, the system 100 can include a surgical fastener 620 with some features analogous to the features of the fastener 120. For example, the fastener 620 includes a head 622 and shank 626 similar to the head 122 and shank 126, respectively, of fastener 120. The fastener 620 shares other features similar to the features of fastener 120, with like numbers referring to like elements. However, the fastener 620 includes some features that are different than the features of the fastener 120. For example, the head 622 includes a single receptacle 624 instead of a plurality of receptacles 124 as with the head 122. Moreover, the single receptacle 624 has a generally circular, ring, or annular shape, as opposed to the generally triangular shape of the receptacles 124.

In the illustrated embodiment, the fastener 620 includes a central bore 650 for receiving a cannulation wire or K-wire. The central bore 650 extends an entire length of the fastener in a coaxial manner relative to a central axis 660 (see, e.g., FIGS. 13 and 14) of the fastener. The receptacle 624 encircles the central bore 650. In embodiments of the fastener 620 without a central bore 650, the receptacle 624 encircles the central axis 660 of the fastener. Generally, the receptacle 624 is formed in an outer or proximal surface 670 of the head 122 and angles radially inwardly in a direction extending away from the outer surface of the head. The receptacle 624 includes a radially inner surface 640 and radially outer surface 642 are both radially inwardly angled in a direction extending away from the outer surface 670 of the head 622 (i.e., in a head-to-shank direction).

Figure 13:
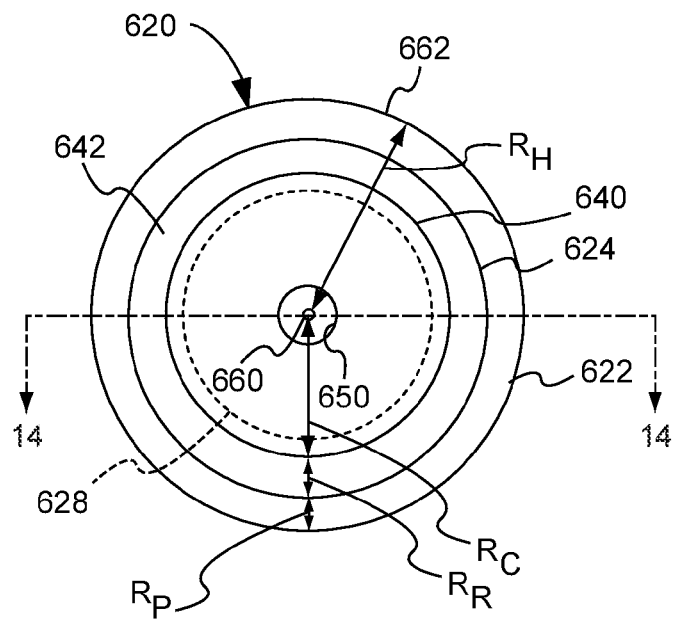
FIG. 13 is a top view of the fastener of FIG. 12.

Referring to FIG. 13, the receptacle 624 is a single, continuous recess or slot extending 360-degrees about the central axis 660 of the fastener 620. The illustrated receptacle 624 is annular, circular, or ring shaped. For example, the intersecting edge between the radially inner surface 640 of the receptacle 624 and the outer surface 670 of the head 622 defines a circle that is concentric with a circle defined by the intersecting edge between the radially outer surface 642 of the receptacle 624 and the outer surface of the head. The opening or inlet of the receptacle 624 is defined as the space between the intersecting edges. Because the radially inner surface 640 is angled radially inwardly, the intersecting edge 628 between the radially inner and outer surfaces 640, 642 defines a radially innermost portion of the receptacle 624.

Although the illustrated receptacle 624 has an annular shape as described above, in other embodiments, the receptacle can have other continuous or circumscribing shapes without departing from the essence of this disclosure. For example, in some embodiments, the receptacle 624 can have a substantially triangular, square, rectangular, or ovular shape. In other words, the intersecting edge between the radially inner surface 640 of the receptacle 624 and the outer surface 670 of the head 622 defines a first shape (e.g., square, rectangle, triangle, oval, and the like) that is concentric with a second shape defined by the intersecting edge between the radially outer surface 642 of the receptacle 624 and the outer surface of the head that corresponds with the first shape. In yet other embodiments, the receptacle 624 can be defined by two non-concentric shapes.

The receptacle 624 is positioned on the outer surface 670 of the head 622 at a location radially inwardly spaced-apart from an outermost periphery 662 of the head and radially outwardly spaced-apart from the central bore 650 and axis 660 of the screw. More specifically, a radial distance $R_P$ is defined between the outer periphery 662 of the head 622 and the intersection of the radially outer surface 642 of the receptacle 624 and the outer surface 670 of the head Likewise, a radial distance $R_C$ is defined between the central axis 660 of the fastener 620 and the intersection of the radially inner surface 640 of the receptacle 624 and the outer surface 670 of the head 622. The radius $R_H$ of the head 622 is equal to the combination of the radial distance $R_P$, the radial distance $R_C$, and a maximum radial thickness $R_R$ of the receptacle 624. The dimensions $R_H$, $R_P$, $R_C$, and $R_R$ can have any of various values and form any of various ratios relative to each other.

Figure 14:
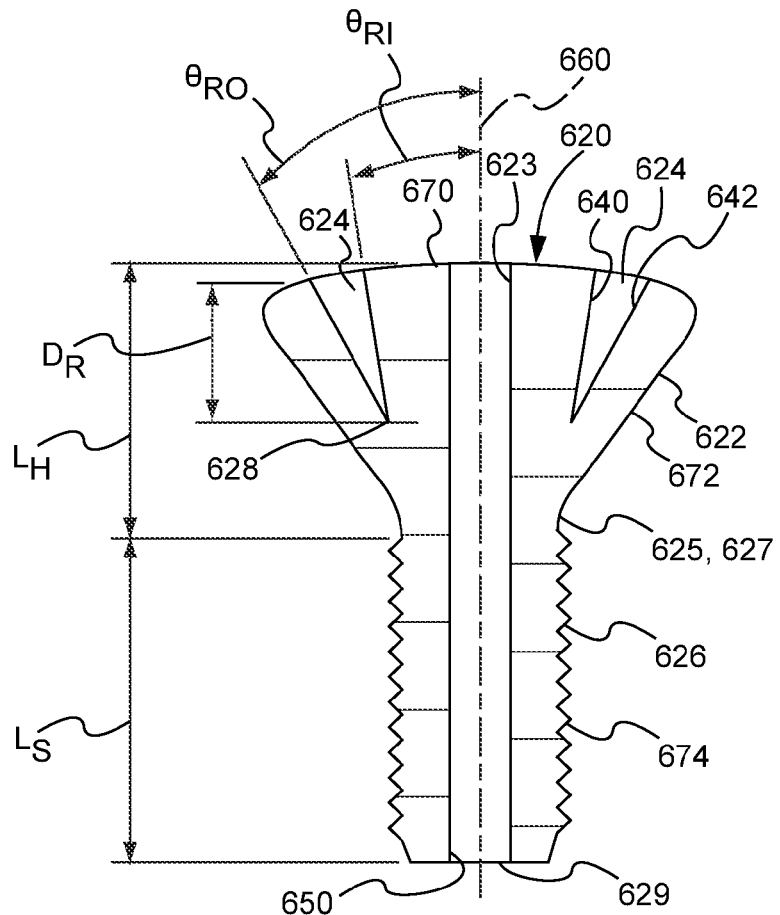
FIG. 14 is a cross-sectional side view of the fastener of FIG. 12 taken along the line 14-14 of FIG. 13.

Due to the radially inward angle of converging of the radially inner and outer surfaces 640, 642, the radial thickness of the receptacle 624 decreases in a direction extending away from the outer surface 670 of the head 622 (see, e.g., FIG. 14). As shown in FIG. 14, the radially inner surface 640 is radially inwardly angled to define a minor angle $\theta_{RI}$ with respect to the central axis 660. Preferably, the receptacle 664 is configured such that the minor angle $\theta_{RI}$ is large enough to keep an installation tool secured to the fastener 620 during installation of the fastener into a material, such as tissue, but small enough to reduce the articulation of the installation tool necessary to secure the fastener (as will be described in more detail below). In some implementations, for example, the minor angle $\theta_{RI}$ is between about 5° and about 20°. In one specific implementation, the minor angle $\theta_{RI}$ is about 10°. The radially outer surface 642 can be inwardly radially angled with respect to the central axis 660 in a manner similar to the radially inner edge 640. More specifically, the radially outer surface 642 defines a minor angle $\theta_{RO}$ with respect to the central axis 660. In some implementations, for example, the minor angle $\theta_{RO}$ is between about 30° and about 80°. In one specific implementation, the minor angle $\theta_{RO}$ is about 60°. Although the illustrated embodiment includes an inwardly radially angled outer surface 642, in other embodiments, the outermost surface 142 of the receptacle 624 is not inwardly angled.

Figure 15:
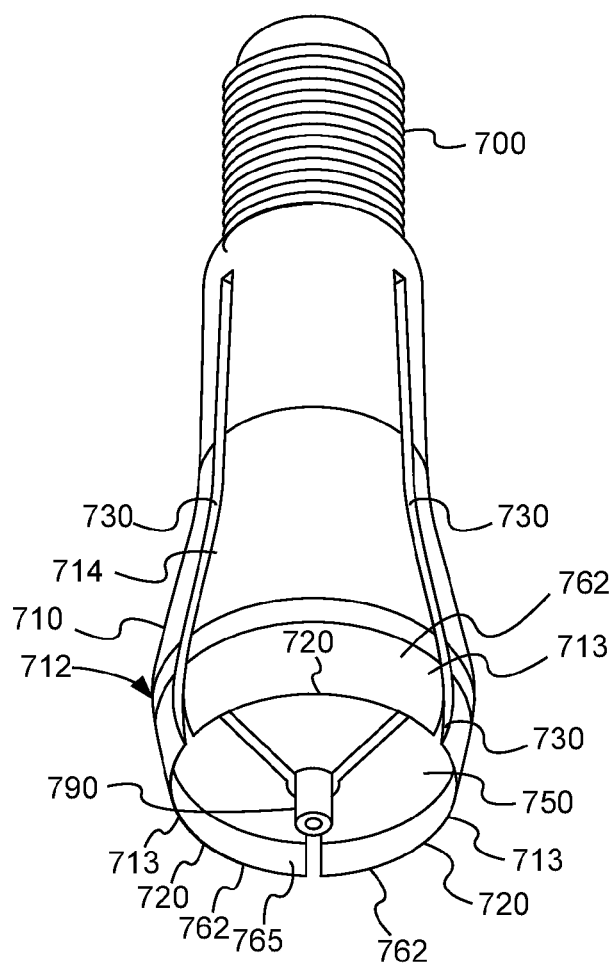
FIG. 15 is a perspective frontal view of a collet of an installation tool according to another embodiment.
Figure 16:
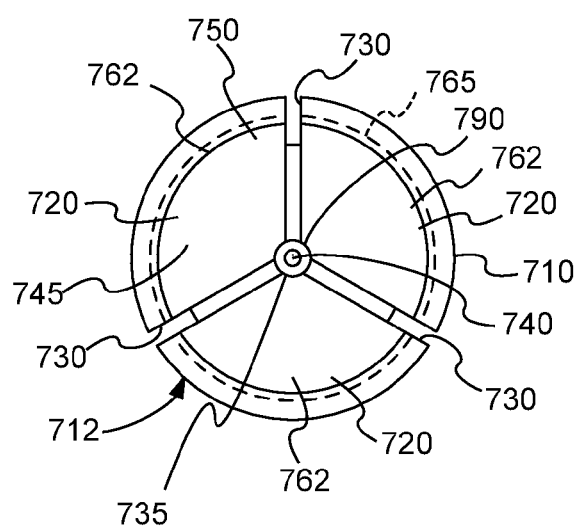
FIG. 16 is a top view of the collet of FIG. 15.

Referring to FIGS. 15 and 16, the system 100 according to another embodiment includes a collet 712 that shares some features analogous to the features of collet 112. The fundamental characteristics of the collet 712 are substantially the same as those of the collet 112 with like numbers referring to like elements. However, the collet 712 is adapted for use with the single receptacle 624 of the fastener 620 instead of the plurality of receptacles 124 of the fastener 120. For example, the collet 712 has a threaded end portion 700 and a compressible end portion 710 generally opposite the threaded end portion. The compressible end portion 710 is resiliently compressible to secure the fastener 620 and decompressible to release the fastener 620.

Like the collet 112, the compressible end portion 710 of the collet 712 includes a plurality of projections 720. However, the projections 720 are sized and shaped differently than the projections 520 of the collet 112. Generally, while the projections 520 define significantly spaced-apart, disparate, radially-aligned teeth, the projections 720 are spaced close together about a periphery of the compressible end portion 710 (e.g., separated only by the width of the longitudinal slits 730) to collectively define a substantially annular projection. In certain implementations, each projection 720 can be defined as having a generally partial-circular, arcuate, and/or crescent shape. The compressible distal end portion 710 of the collet 712 includes a plurality of cantilevered sections 713 each movable relative to each other. Each section 713 includes a respective one of the projections 520. In certain implementations, the sections are compressible toward and into contact with each other to form a continuous annular projection.

In certain embodiments, the projections 720 have the same cross-sectional shape and size as the receptacle 624. More specifically, each projection 720 includes a radially inner surface 765 that corresponds with the radially inner surface 640 of the receptacle 624 such that the projections 720 are matingly engageable with (e.g., insertable within and/or nestably engageable with) the receptacle 624. More specifically, the radially inner surfaces 765 of the projections 720 are inwardly angled with respect to the central axis 740 of the collet 712. In certain embodiments, the minor angle defined between the respective radially inner surfaces 765 and the central axis 740 is substantially the same as the minor angle $\theta_{RO}$ defined between the radially inner surface 640 and the central axis 660 of the fastener 620. Each projection 720 also includes a radially outer surface 765 that corresponds with the radially outer surface 642 of the receptacle 624. The radially outer surfaces 765 can be inwardly angled with respect to the central axis 740 of the collet 712. In certain implementations, the minor angle defined between the respective radially outer surfaces 765 and the central axis 740 is substantially the same as, or less than, the minor angle $\theta_{RO}$ defined between the radially inner surface 640 and the central axis 660 of the fastener 620.

Although in the illustrated embodiments, the compressible end portion 710 of the collet 712 includes three sections 713 and three projections 720 each associated with a respective section, in other embodiments, the collet 712 can have two or more than three sections and two or more than three projections. In some implementations, each section 713 can include more than one projection 720 if desired. For example, in the illustrated embodiment, each projection 720 extends about an entire periphery of a respective section. However, if desirable, multiple similarly-shaped projections 720 can be used on each section 713 instead of a single projection on the section.

The collet 712 also includes a cantilevered alignment rod 790 positioned within and extending coaxially with the central bore 735. A distal end (e.g., free end) of the alignment rod 790 proximate the compressible end portion 710 extends distally away from the distal end surface 750. A proximal end (e.g., fixed end) of the alignment rod 790 is coupled to the threaded end portion 700. The alignment rod 790 is freely movable within the central bore 735 relative to the sections 513 of the compressible end portion 710.

The fastener 620 is secured to the installation tool 110 in a manner similar to that described above with reference to FIG. 11. For example, the projections 720 of the collet 712 in an uncompressed state are positioned at least partially within the receptacle 624. However, unlike the plurality of receptacles 124 and projections 520 arrangement associated with fastener 120 and collet 112, rotational alignment between the receptacle 624 and projections 720 for proper insertion of the projections into the receptacle 624 is not necessary. In other words, because the receptacle 624 is an endless receptacle, the projections 720 can be properly inserted into the receptacle 624 at any of various rotational orientations of the fastener 620 and collet 712 relative to the respective central axes 660, 740. Such rotational orientation independency improves the ease and simplicity of securing the fastener 620 to the collet 712.

After positioning the projections 720 at least partially within the receptacle 624, the sections 713 of the compressible distal end portion 710 are compressed inwardly toward each other by adjusting the tightening portion of the installation tool 110. As the compressible distal end portion 510 compresses, engagement between the radially inner surfaces 640, 765 of the receptacle 624 and projections 720, respectively, urges the fastener 620 toward the collet 712 to securely and fully seat the projections within the receptacle. The projections 720 apply an additional compressive and retention force against the receptacle 624 by adjusting the locking portion of the installation tool as discussed above. The final compressive and retention force is sufficient to ensure co-rotation of the fastener 620 and installation tool 110 (including the collet 712) during the installation of the fastener into a material (e.g., biological tissue or bone). After tightening the projections 720 against the receptacle 624, the angled nature of the radially inner surfaces 640, 765 of the receptacle 624 and projections 720, respectively, the fastener 620 is prevented from disengagement with the collet 712 while the collet remains compressed.

Desirably, manual contact with the fastener during the installation procedure is avoided to reduce the likelihood of contamination of and/or damage to the fastener. According to one method, a fastener of the present disclosure is securable to an installation tool and drivable into a material at a surgical site without manual contact with the fastener. Prior to installation of a surgical fastener into biological material, the fastener is sterilized and positioned in a sterilized environment (e.g., on a sterilized tray) preparatory for the installation procedure. A medical professional manually grasps the installation tool with a collet coupled thereto and positions the installation tool such that the projections of the collet are partially inserted into the receptacle(s) of the sterilized faster without touching the fastener. With the projections within the receptacle(s), the installation tool is manually tightened to compress the collet against the receptacle(s) and secure the fastener to the installation tool. The installation tool (with the secured fastener) is moved to the surgical site and oriented to position the fastener above the installation point at the desired angle. The medical profession then drives the fastener into the biological material by articulating (e.g., rotating) the installation tool.

To facilitate coaxial alignment between the fastener 620 and the collet 712 while securing the fastener to the collet and installing the fastener into a material, the alignment rod 790 of the collet is positionable within the central bore 650 of the fastener. Engagement between the alignment rod 790 and the central bore 650 acts to maintain the fastener 620 and collet 712 in coaxial (e.g., vertical) alignment while positioning the projections 720 in the receptacle 624, compressing the collet 712 against the fastener, and driving the fastener into the material.

The present subject matter may be embodied in other specific forms without departing from its spirit or essential characteristics. The described embodiments are to be considered in all respects only as illustrative and not restrictive. The scope of the subject matter is, therefore, indicated by the appended claims rather than by the foregoing description. All changes which come within the meaning and range of equivalency of the claims are to be embraced within their scope.

What is claimed is:

1. A fastener, comprising:
   a shank defined about a central axis; and
   a head coupled to the shank, the head comprising a continuous receptacle circumscribing the central axis, wherein the continuous receptacle comprises a radially inner surface angled radially inwardly toward the central axis in a head-to-shank direction, and wherein the continuous receptacle comprises an annular shape.

2. The fastener of claim 1, wherein the continuous receptacle comprises a radially outer surface angled radially inwardly toward the central axis in the head-to-shank direction.

3. The fastener of claim 1, wherein the continuous receptacle is located on the head between the central axis and an outer periphery of the head.

4. The fastener of claim 1, wherein the continuous receptacle comprises an opening defined between a first circular edge formed in the head and a second circular edge formed in the head, the first and second circular edges defining concentric circles.

5. A fastener and installation tool system, comprising:
   a fastener comprising:
      a shank defined about a central axis; and
      a head coupled to the shank, the head comprising a continuous receptacle circumscribing the central axis, wherein the continuous receptacle comprises a radially inner surface angled radially inwardly toward the central axis in a head-to-shank direction; and
   an installation tool comprising:
      a flexible collet comprising a proximal end and a distal end, the distal end comprising a plurality of projections each matingly engageable with the continuous receptacle;
      a collet flexing portion engageable with the collet to flex the collet to draw the plurality of projections radially inward toward each other.

6. The system of claim 5, wherein the continuous receptacle comprises an annular shape and the plurality of projections each comprises an arcuate shape.

7. The system of claim 6, wherein when radially inwardly drawn toward each other, the plurality of projections collectively define an annular shape corresponding to the annular shape of the continuous receptacle.

8. The system of claim 5, wherein the fastener comprises a central bore extending through the shank and head, and wherein the flexible collet comprises an alignment rod engageable with the central bore to align the fastener and the flexible collet.

9. The system of claim 5, wherein the plurality of projections are matingly engageable with the continuous receptacle independently of the relative rotational orientation of the fastener and flexible collet.

10. The system of claim 5, wherein the plurality of projections are positioned about a periphery of the proximal end of the flexible collet.

11. The system of claim 5, wherein each of the projections comprises a radially inner surface extending radially outwardly in a direction away from the distal end of the collet toward the proximal end of the collet.

12. A fastener, comprising:
    a shank concentrically aligned with a central axis of the fastener; and
    a head coupled to the shank, wherein the head extends from a proximal end to a distal end, and the shank extends from a proximal end adjacent the distal end of the head to a distal end away from the distal end of the head, the head comprising at least one receptacle spaced radially outwardly away from the central axis of the fastener, wherein a radially innermost portion of the at least one receptacle extends radially inwardly toward the central axis in a direction away from the proximal end of the head;
    wherein the at least one receptacle comprises an annular-shaped receptacle.

13. The fastener of claim 12, wherein the at least one receptacle circumscribes the central axis.

14. The fastener of claim 12, wherein the radially innermost portion of the at least one receptacle forms a minor angle with the central axis of the fastener of at least 5°.

15. The fastener of claim 14, wherein the radially innermost portion of the at least one receptacle forms a minor angle with the central axis of the fastener of at least 10°.

16. The fastener of claim 12, wherein the at least one receptacle is spaced radially inward from an outer periphery of the head, the outer periphery being defined along a plane perpendicular to the central axis.

17. The fastener of claim 12, wherein the radially innermost portion of the at least one receptacle forms a minor angle with the central axis of the fastener of at least 5° and an outermost portion of the at least one receptacle forms a minor angle with the central axis of the fastener of at least 10°.

18. The fastener of claim 12, wherein the at least one receptacle has a substantially triangular-shaped cross-section defined along a plane parallel to the central axis of the fastener.

* * * * *